United States Patent
Reuther et al.

[11] Patent Number: 6,069,161
[45] Date of Patent: May 30, 2000

[54] USE OF AMINOISOTHIAZOLES AS MICROBICIDES

[75] Inventors: Wolfgang Reuther, Heidelberg; John-Bryan Speakman, Bobenheim; Dieter Zeller, Wiesloch, all of Germany

[73] Assignee: BASF Aktiengesellschaft, Ludwigshafen, Germany

[21] Appl. No.: 09/331,067

[22] PCT Filed: Dec. 9, 1997

[86] PCT No.: PCT/EP97/06854

§ 371 Date: Jun. 16, 1999

§ 102(e) Date: Jun. 16, 1999

[87] PCT Pub. No.: WO98/27816

PCT Pub. Date: Jul. 2, 1998

[30] Foreign Application Priority Data

Dec. 23, 1996 [DE] Germany .......................... 196 54 147

[51] Int. Cl.⁷ ........................... A01N 43/36; A01N 43/80
[52] U.S. Cl. .......................... 514/372; 504/156
[58] Field of Search ............... 514/372; 504/156

[56] References Cited

U.S. PATENT DOCUMENTS

| | | | |
|---|---|---|---|
| 4,032,322 | 6/1977 | Gibbons | 71/90 |
| 4,396,413 | 8/1983 | Miller et al. | 71/67 |
| 5,538,939 | 7/1996 | Muenster et al. | 504/269 |

FOREIGN PATENT DOCUMENTS 640 597  3/1995  European Pat. Off. .

OTHER PUBLICATIONS

Pol. J. Pharm. 1984, 36, 485–491, Kuczynski et al.
Pest. Sci. 1992, 34, 127–131, Vicentini et al.
Synthesis of some 4–Nitroisothiazoles . . . , Albert et al., Mar. 1980, 385–387.

*Primary Examiner*—Allen J. Robinson
*Attorney, Agent, or Firm*—Keil & Weinkauf

[57] ABSTRACT

Aminoisothiazoles of the formula I,

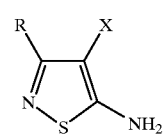

where
R is hydrogen or $C_1$–$C_4$ alkyl and
X is halogen, $NO_2$, CN or SCN, and metal complexes and acid addition salts thereof
are used as microbicides for protecting industrial materials from being attacked and destroyed by microorganisms.

6 Claims, No Drawings

USE OF AMINOISOTHIAZOLES AS MICROBICIDES

This application is a 371 of PCT/EP97/06854, filed Dec. 9, 1997.

The present invention relates to the use of aminoisothiazoles as microbicides for protecting industrial materials from being attacked and destroyed by microorganisms. Furthermore, the invention relates to a method for protecting industrial materials from being attacked and destroyed by microorganisms.

Isothiazoles (U.S. Pat. No. 3,761,488, U.S. Pat. No. 4,105,431, U.S. Pat. No. 4,252,694, U.S. Pat. No. 4,265,899, U.S. Pat. No. 4,279,762, U.S. Pat. No. 5,430,046, EP-A 697 409) and benzothiophene derivatives (DE-A 44 11 912), and also mixtures of specific azole derivatives with ammonium compounds (EP-A 533 016), are known to have microbicidal properties. The preparation of some of these compounds is very complicated and their efficacy in particular at low application rates is not always satisfactory.

5-Aminoisothiazoles have been described as coupling components in azo dyes (EP-A 362 708, EP-A 315 898). 5-Aminoisothiazoles (in many cases N-acylated) are also known to have herbicidal (EP-A 640 597, DE-A 24 34 922, DE-A 22 49 162, FR 2132691, U.S. Pat. No. 4,032,321, U.S. Pat. No. 4,032,322, ZA 7202352), bactericidal and virucidal activity (L. Kuczynski et al., Pol. J. Pharmacol. Pharm. (1984), 36(5), 485–491), and to be useful as intermediates for drugs and crop protecting agents.

It is an object of the present invention to provide compounds which can be used as microbicides in the protection of materials, are easily accessible and have a good microbicidal activity.

We have found that this object is achieved by the 5-aminoisothiazoles of the formula I,

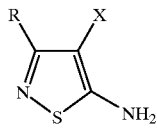

I where
R is hydrogen or $C_1$–$C_4$-alkyl and
X is halogen, $NO_2$, CN or SCN, and metal complexes and acid addition salts thereof which are very suitable for use as microbicides in the protection of materials. Preference is given to compounds where
R is $C_1$–$C_4$-alkyl, in particular methyl.
Furthermore, preference is given to compounds where
X is CN and in particular SCN.

In a particularly preferred embodiment, 3-methyl-4-thiocyanato-5-aminoisothiazole (formula Ic),

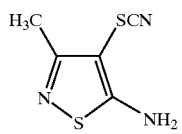

Ic and metal complexes and acid addition salts thereof are used.

The compounds I suitable for use according to the invention are obtained by a reaction sequence known per se from EP-A-640 597 by converting isothiazoles of the general formula II,

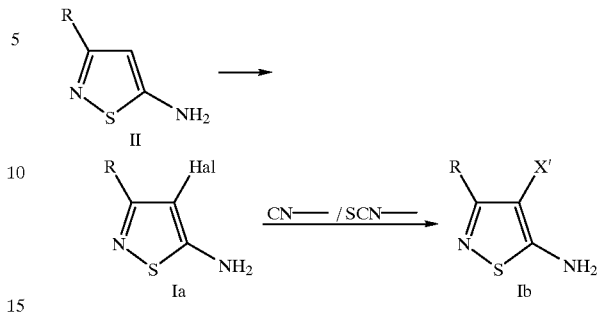

with the aid of a halogenating agent into the halo compound Ia, where Hal is F, Cl, Br, or I, which is then, if required, converted into the compound Ib, where X' is SCN or CN, by reaction with thiocyanates or cyanides. The preparation of isothiazoles of the general formula II is described for example in DE-A-17 70 819. The preparation of 3-methyl-5-aminoisothiazole was described by A. Adams et al. in J. Chem. Soc. 1959, p. 3061.

The aminoisothiazoles I, per se or in a formulation, are suitable for protecting industrial materials from being attacked and destroyed by microorganisms.

Industrial materials are non-living materials as obtained in industrial processes or non-living materials intended for use in industry. Industrial materials to be protected by the active compounds I from being altered or destroyed by microbes are, for example, dispersions, adhesives, glues, cosmetics, starch solutions, wax emulsions, clay emulsions, paper, sizes, finishes, spin baths, textiles, leather, raw hides, gelatin preparations, bedding putty, joint fillers, wood, paints, articles made from plastic, coolants, drilling oils and other materials which can be attacked or decomposed by microorganisms. The compounds are further suitable for use as slimicides in the paper industry, in recooling plants and air humidifiers. The aminoisothiazoles I are particularly preferably employed in dispersions, such as polymer dispersions and paints.

Microorganisms which may cause a decomposition or an alteration of the industrial materials are, for example, spores, viruses, bacteria, fungi, yeasts, algae and slime organisms. The active compounds or preparations according to the invention preferably act against fungi, bacteria and algae.

By way of example, microorganisms of the following varieties may be mentioned:

*Alternaria alternata, Alternaria tenuis, Aspergillus niger, Aureobasidium pullulans, Candida albicans, Chaetomium globosum, Citrobacter freundii, Cladosporium resinae, Coniophora puteana, Desulfovibrio desulfuricans, Escherichia coli, Klebsiella pneumoniae, Lentinus tigrinus, Penicillium expansum, Penicillium funiculosum, Penicillium glaucum, Polyporus versicolor, Proteus mirabilis, Proteus vulgaris, Pseudomonas aeruginosa, Sclerophoma pityophila, Saccharomyces cerevisiae, Staphylococcus aureus, Streptoverticillium rubrireticuli, Trichoderma viride.*

Depending on their physical and chemical properties and on the desired application, the active compounds of the formula I can be converted into customary formulations, for example solutions, emulsions, powders, pastes or dispersions.

These active compound formulations are prepared in a conventional manner, for example by mixing the active compounds with suitable extenders or solvents, if required by employing surface-active agents, i.e. emulsifiers or dispersants. If water is used, organic solvents are generally employed as auxiliary solvents. Suitable solvents are, for example, alcohols, such as methanol, ethanol, propanol, butanol and cyclohexanol, or glycols, such as propylene glycol, 2-phenoxyethanol, phenoxypropanol, or aliphatic, cyclic and aromatic hydrocarbons, such as toluene, xylene, mesitylene, paraffin, tetrahydronaphthalene, alkylated naphthalenes or derivatves thereof, chlorobenzene, dichlorobenzene or strongly polar solvents, such as N,N-dimethylformamide, N,N-dimethylacetamide, dimethyl sulfoxide or N-methylpyrrolidone.

Suitable emulsifiers are, for example, alkali metal salts, alkaline earth metal salts or ammonium salts of aromatic sulfonic acids, for example of lignosulfonic acid, phenolsulfonic acid, naphthalenesulfonic acid and dibutylnaphthalenesulfonic acid, and of fatty acids, alkyl- and arylsulfonates, alkyl sulfates, lauryl ether sulfates and fatty alcohol sulfates, and salts of sulfated hexadecanols, heptadecanols and octadecanols, and condensation products of sulfonated naphthalene or naphthalene derivatives with formaldehyde, condensation products of naphthalene or of naphthalenesulfonic acids with phenol and formaldehyde, polyoxyethylene fatty alcohol ethers, polyoxyethylene octyl phenol ethers, ethoxylated isooctylphenol, ethoxylated octylphenol or ethoxylated nonylphenyl, alkylphenyl polyglycol ethers, tributylphenyl polyglycol ethers, isotridecyl alcohol, alkylaryl polyglycol ethers, ethoxylated castor oil, polyoxyethylene alkyl ethers or polyoxypropylene, lauryl alcohol polyglycol ether acetate, sorbitol esters; suitable dispersants are, for example, ligno-sulfite waste liquors and methylcellulose.

Aliphatic carboxylic acids may be added to improve the homogeneity of the concentrates. Such acids are, for example, propionic acid, hexanoic acid, heptanoic acid, branched carboxylic acids, such as 2-ethylenehexanoic acid, isooctanoic acid, neocarboxylic acids, aliphatic dicarboxylic acids, such as sebacic acid, cycloalkylcarboxylic acids, such as cyclohexanoic acid, arylcarboxylic acids, such as benzoic acid, 3- or 4-hydroxybenzoic acid.

Paints or precursors for preparing paints include plastic dispersions, dispersion paints for the paint industry, starch solutions, suspensions of other raw materials, such as color pigments or dyes or suspensions of fillers, such as kaolin, calcium carbonate, silicic acids, silica gels, silicates, talc, limestone, lime, chalk, bole, loess, clay, dolomite, diatomaceous earth, calcium sulfate and magnesium sulfate, magnesium oxide or ground plastics.

The activity and the spectrum of activity of the active compounds of the formula I or the compositions, intermediates or formulations preparable therefrom can be increased by adding further, optionally antimicrobially active compounds, bactericides, fungicides, herbicides, insecticides or other active compounds for widening the spectrum of activity or obtaining special effects. In many instances, this results in synergistic effects, i.e. the spectrum of activity of the mixture is superior to the activity of the individual components.

Particularly advantageous mixing partners are, for example:
microbicides:
2-(thiocyanatomethylthio)benzothiazole, 1-[2-(2,4-dichlorophenyl)-2-(2-propenyl-oxy)ethyl]-1H-imidazole, 2,4,5,6-tetrachloroisophthalodinitrile, methylene bisthiocyanate, tributyltin oxide, tributyltin naphthenate, tributyltin benzoate, tributyltin salicylate, mercaptobenzothiazole, 1,2-benzisothiazolone and its alkali metal salts, alkali metal compounds of N'-hydroxy-N-cyclohexyldiazenium oxide, 2-(methoxycarbonylamino) benzimidazole, 2-methyl-3-oxo-5-chlorothiazolin-3-one, trihydroxymethylnitromethane, glutaraldehyde, chloroacetamide, polyhexamethylenebisguanides, 5-chloro-2-methyl-4-isothiazolin-3-one+magnesium salts, 2-methyl-4-isothiazolin-3-one, 3,5-dimethyltetrahydro-1,3,4-2H-thiadiazin-2-thione, hexahydrotriazine, N,N-methylolchloroacetamide, 2-n-octyl-4-isothiazolin-3-one, oxazolidines, bisoxazolidines, 5-dihydro-2,5-dialkoxy-2,5-dialkylfurans, diethyldodecylbenzylammonium chloride, dimethyloctadecyldimethylbenzylammonium chloride, dimethyldidecylammonium chloride, dimethyldidodecylammonium chloride, trimethyltetradecylammonium chloride, benzyldimethylalkyl-($C_{12}$–$C_{18}$)-ammonium chloride, dichlorobenzyldimethyldodecylammonium chloride, cetylpyridinium chloride, cetylpyridinium bromide, cetyltrimethylammonium chloride, laurylpyridinium chloride, laurylpyridinium bisulfate, benzyldodecyldi(beta-oxyethyl) ammonium chloride, dodecylbenzyltrimethylammonium chloride, n-alkyldimethylbenzylammonium chloride (alkyl radical: 40% $C_{12}$, 50% $C_{14}$, 10% $C_{16}$), lauryldimethylethylammonium ethyl sulfate, n-alkyldimethyl(1-naphthylmethyl)ammonium chloride (alkyl radical: 98% $C_{12}$, 2% $C_{14}$), cetyldimethylbenzylammonium chloride, lauryldimethylbenzylammonium chloride, Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulfate and other copper preparations, Fungicides:
sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediamine-bis-dithiocarbamate, tetramethylthiuram disulfide, ammonia complex of zinc (N,N-ethylene-bis-dithiocarbamate), ammonia complex of zinc (N,N'-propylene-bis-dithiocarbamate), zinc (N,N'-propylenebisdithiocarbamate), N,N'-polypropylenebis (thiocarbamoyl) disulfide;

nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis (dimethylamino)phosphinyl]-3-phenyl-1,2,4-triazole, 2,3-dicyano-1,4-dithioanthraquinone, 2-thio-1,3-dithiolo[4,5-b] quinoxaline, methyl 1-(butylcarbamoyl)-2-benzimidazolecarbamate, 2-methoxycarbonylaminobenzimidazole, 2-(furyl-(2)) benzimidazole, 2-(thiazolyl-(4))benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine-4,4- dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethylacetal, piperazine-1,4-diylbis-(1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, (2-chlorophenyl)-(4-chlorophenyl)-5-pyrimidine-methanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, [2-(4-chlorophenyl)ethyl]-(1,1-dimethylethyl)-1H-1,2,4-triazole-1-ethanol, 1-[3-(2-chlorophenyl)-1-(4-fluorophenyl)oxiran-2-ylmethyl]-1H-1,2,4-triazole, and
a variety of fungicides, such as dodecylguanidine acetate, 3-[3-(3,5-dimethyl-2-oxycyclohexyl)-2-hydroxyethyl] glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(-5-methyl-5-methoxymethyl]-1,3-oxazolidine-2,4-dione, 3-(3,5-dichlorohenyl)-1-isopropylcarbamoyl-hydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-a-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis-(4-fluorophenyl) methylsilyl)methyl)-1H-1,2,4-triazole.

Strobilurins, such as methyl E-methoximino-[a-(o-tolyloxy)-o-tolyl]acetate, methyl E-2-{2-[6-(2-cyanophenoxy)pyridimin-4-yloxy]phenyl}-3-methoxyacrylate, methyl-E-methoximino-[a-(2-phenoxyphenyl)] acetamide, methyl-E-methoximino-[a-(2,5-dimethylphenoxy)-o-tolyl]acetamide.

Anilinopyrimidines, such as N-(4,6-dimethylpyrimidin-2-yl)aniline, N-[4-methyl-6-(1-propynyl)pyrimidin-2-yl] aniline, N-(4-methyl-6-cyclopropylpyrimidin-2-yl)aniline.

Phenylpyrroles, such as 4-(2,2-difluoro-1,3-benzodioxol-4-yl)pyrrole-3-carbonitrile.

Cinnamamides, such as 3-(4-chlorophenyl)-3-(3,4-dimethoxyphenyl)acryloylmorpholide. (2RS,3SR)-1-[3-(2-chlorophenyl)-2-[4-fluorophenyl]oxiran-2-yl methyl]-1H-1,2,4-triazole.

Insecticides:
abamectin, acephate, acrinathrin, alanycarb, aldicarb, alphamethrin, amitraz, avermectin, azadirachtin, azinphos A, azinphos M, azocyclotin, bacillus thuringiensis, bendiocarb, benfuracarb, bensultap, beta-cyluthrin, bifenthrin, BPMC, brofenprox, bromophos A, butencarb, buprofezin, butocarboxin, butylpyridaben, cadusafor, carbaryl, carbofuran, carbophenothion, carbosulfan, cartap, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cypromazin, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivemectin, lamda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, nitenpyram, omethoate, oxamyl, oxydemethone M, oxydeprofos, parathion A, parathion M, permethrin, phenthoate, phorate, phosalone, phosmet, phosphamdon, phoxim, pirimicarb, pirimiphos M, primiphbs A, profenofos, promecarb, propaphos, propoxur, prothiofos, prothiophos, prothoate, pymetrozine, pyraclofos, pyradaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimfos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, zetamethrin.

Further suitable mixing partners are algicides, molluscicides, and active compounds against sea animals which colonize, for example, ship's bottom paints.

Examples of such preparations are:

1. Examples of formulations in dispersion paints or plastic dispersions:
   a) 1000 parts by weight of a polymer dispersion based on polyacrylate are initially introduced and admixed with stirring with 0.25 parts by weight of a 20% strength by weight suspension concentrate of 3-methyl-4-thiocyanato-5-aminoisothiazole in propylene carbonate.
   b) It is possible to add the pulverulent active compound to the ready-made-up dispersion.
   c) A solution of 3% by weight of 3-methyl-4-thiocyanato-5-aminoisothiazole in propylene glycol, dipropylene glycol, phenoxyethanol, phenoxypropanol or polyethylene glycol is suitable for incorporation into aqueous and solvent-containing plastic dispersions.
   d) A water- or glycol-based paste containing 20 to 50% by weight of 3-methyl-4-thiocyanato-5-aminoisothiazole is suitable for incorporation into aqueous and solvent-containing plastic dispersions.
   e) A solution of 90 parts by weight of 3-methyl-4-thiocyanato-5-aminoisothiazole and 10 parts by weight of N-methylpyrrolidone is suitable for incorporation into aqueous and solvent-containing plastic dispersions.

f) An aqueous dispersion of 20 parts by weight of 3-methyl-4-thiocyanato-5-aminoisothiazole, 25 parts by weight of cyclohexanol, 65 parts by weight of a mineral oil fraction of boiling point 210–280° C. and 10 parts by weight of the addition product of 40 mols of ethylene oxide to 1 mol of castor oil. The mixture of this dispersion with 100,000 parts by weight of an aqueous paint dispersion comprises 0.02% of the active compound.

2. A mixture of 14 parts by weight of $Cu(OH)_2CuCO_3$, 33 parts by weight of monoethanolamine, 22 parts by weight of benzoic acid, 11 parts by weight of water, 4 parts by weight of 3-methyl-4-thiocyanato-5-aminoisothiazole, 10 parts by weight of ethoxylated nonylphenol and 6 parts by weight of propylene glycol is particularly suitable for impregnating wood.

The microbicidal compositions or concentrates employed for protecting industrial materials comprise the active compound or the active compound combination in a concentration from 0.01 to 95, preferably 0.1 to 50,% by weight.

The application concentration of the active compounds to be used depends on the species and the occurrence of the microorganisms to be controlled, and on the composition of the material to be protected. The application concentrations are generally in the range from 0.001 to 5% by weight, preferably from 0.05 to 1% by weight, based on the material to be protected.

The following examples illustrate the invention:
Biological Examples:
1. Microtiter plate test—1000, 500 and 250 ppm The active compound Ic was dissolved in acetone. 100 µl of a culture medium were placed in the wells of microtiter plates and aliquots of the active compound stock solution were pipetted in to give the desired test concentration. The final acetone concentration was 10%. Test microorganisms used were (bacteria) *Citrobacter freundii, Escherichia coli, Proteus mirabilis, Pseudonomas aeruginosa* and *Staphylococcus aureus* (yeasts) *Candida albicans* and *Saccharomyces cerevisiae,* and (fungi) *Alternaria alternata, Aspergillus niger* and *Penicillium funiculosum.* The innoculated plates were incubated at 23° C. (yeasts and fungi) or 30° C. (bacteria). The growth of the microorganisms was evaluated after 2 (bacteria), 3 (yeasts) or 5 days (fungi):

| Test organism | Concentration in ppm active substance (a.s.) | | |
| --- | --- | --- | --- |
| | 1000 | 500 | 250 |
| *Citrobacter freundii* | 0 | 0 | 5 |
| *Escherichia coli* | 0 | 0 | H |
| *Proteus mirabilis* | 0 | 0 | 0 |
| *Pseudomonas Aeruginosa* | 0 | 0 | 0 |
| *Staphylococcus aureus* | H | H | H |
| *Candida albicans* | 0 | 0 | H |
| *Saccharomyces cerevisiae* | 0 | 0 | H |
| *Alternaria alternate* | 0 | 0 | 0 |
| *Aspergillus niger* | 0 | 0 | 0 |
| *Penicillium funiculosum* | 0 | 0 | 0 |
| Control | 5 | 5 | 5 |

0 = no growth
H = inhibition of growth
5 = no action, growth as in the control

2. Preservation stress test in a polymer dispersion based on polyacrylate.

In-depth tests were carried out in a polymer dispersion based on polyacrylate. The active compound Ic was dissolved in acetone and admixed to the dispersion in concentrations of 500, 250 and 100 ppm of a.s. The dispersions were then inoculated ("stressed") with a mixture of microorganisms. The mixture comprised the microorganisms mentioned under point 1. The experiments were incubated at 23° C. and inoculated again every 7 days. After 6 cycles, the microorganism content of the dispersion was determined.

It was found that the polymer dispersion could be kept free of microorganisms using an application concentration of 250 ppm of a.s.

We claim:

1. A method for protecting industrial materials from being attacked and destroyed by microorganisms which comprises treating said materials with an effective amount of a aminoisothiazole microbicide of the following formula I

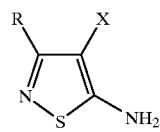

wherein

R is hydrogen or $C_1$–$C_4$-alkyl and

X is halogen, $NO_2$, CN or SCN, or metal complexes or acid addition salts thereof.

2. The method of claim 1, wherein the aminoisothiazole of the formula I or metal complexes or acid addition salts thereof is admixed with an inert carrier material and, optionally, a surfactant.

3. The method as claimed in claim 1, wherein

R is $C_1$–$C_4$-alkyl and

X is CN and SCN.

4. The method as claimed in claim 1, wherein

R is methyl.

5. The method as claimed in claim 1, wherein X in the formula I is thiocyanato.

6. The method as claimed in claim 1, wherein 3-methyl-4-thiocyanato-5-aminoisothiazole (formula Ic) is used.

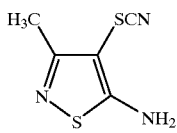

* * * * *

UNITED STATES PATENT AND TRADEMARK OFFICE
CERTIFICATE OF CORRECTION

PATENT NO.: 6,069,161

DATED: May 30, 2000

INVENTOR(S): REUTHER et al.

It is certified that error appears in the above-identified patent and that said Letters Patent is hereby corrected as shown below:

Col. 8, claim 1, lines 20 and 21, delete "ami-noisothiazole".

Signed and Sealed this

Twenty-fourth Day of April, 2001

Attest:

NICHOLAS P. GODICI

Attesting Officer

Acting Director of the United States Patent and Trademark Office